US011208582B2

(12) United States Patent
Pham et al.

(10) Patent No.: US 11,208,582 B2
(45) Date of Patent: Dec. 28, 2021

(54) AZEOTROPE OR AZEOTROPE-LIKE COMPOSITIONS OF TRIFLUOROIODOMETHANE ($CF_3I$) AND TRIFLUOROACETYL CHLORIDE ($CF_3COCl$)

(71) Applicant: Honeywell International Inc., Morris Plains, NJ (US)

(72) Inventors: Hang T. Pham, Amherst, NY (US); Ryan J. Hulse, Getzville, NY (US); Rajiv Ratna Singh, Getzville, NY (US); Haridasan K. Nair, Williamsville, NY (US)

(73) Assignee: Honeywell International Inc., Charlotte, NC (US)

( * ) Notice: Subject to any disclaimer, the term of this patent is extended or adjusted under 35 U.S.C. 154(b) by 0 days.

(21) Appl. No.: 16/874,319

(22) Filed: May 14, 2020

(65) Prior Publication Data

US 2020/0369933 A1 Nov. 26, 2020

Related U.S. Application Data

(60) Provisional application No. 62/850,378, filed on May 20, 2019.

(51) Int. Cl.
| | |
|---|---|
| *C09K 5/04* | (2006.01) |
| *B01D 3/36* | (2006.01) |
| *C07C 53/48* | (2006.01) |
| *C07C 19/16* | (2006.01) |

(52) U.S. Cl.
CPC .............. *C09K 5/045* (2013.01); *B01D 3/36* (2013.01); *C07C 19/16* (2013.01); *C07C 53/48* (2013.01)

(58) Field of Classification Search
CPC ....... C03B 19/12; C07C 51/64; C07C 17/383; C07C 53/48; C07C 19/16
See application file for complete search history.

(56) References Cited

U.S. PATENT DOCUMENTS

| | | | |
|---|---|---|---|
| 10,954,177 B2 * | 3/2021 | Nair | ......................... B01J 23/72 |
| 2005/0233923 A1 | 10/2005 | Singh et al. | |
| 2008/0135817 A1 | 6/2008 | Luly et al. | |
| 2011/0295045 A1 | 12/2011 | Hulse et al. | |

FOREIGN PATENT DOCUMENTS

| | | |
|---|---|---|
| WO | 2009/105517 A2 | 8/2009 |
| WO | 2017/029499 A1 | 2/2017 |

* cited by examiner

*Primary Examiner* — Jafar F Parsa (74) *Attorney, Agent, or Firm* — Faegre Drinker Biddle & Reath LLP (57) ABSTRACT

The present disclosure provides azeotrope or azeotrope-like compositions including trifluoroiodomethane ($CF_3I$) and trifluoroacetyl chloride ($CF_3COCl$), and a method of forming an azeotrope or azeotrope-like composition comprising the step of combining trifluoroacetyl chloride ($CF_3COCl$) and trifluoroiodomethane ($CF_3I$) to form an azeotrope or azeotrope-like composition.

19 Claims, 3 Drawing Sheets

Figure 1: Ebulliometer study of CF3I/CF3COCl at P = 14.4 psia

AZEOTROPE OR AZEOTROPE-LIKE COMPOSITIONS OF TRIFLUOROIODOMETHANE ($CF_3I$) AND TRIFLUOROACETYL CHLORIDE ($CF_3COCl$)

CROSS-REFERENCE TO RELATED APPLICATIONS

This application claims priority to U.S. Provisional Application No. 62/850,378, filed May 20, 2019, which is herein incorporated by reference in its entirety.

FIELD

The present disclosure is related to azeotrope or azeotrope-like compositions and, in particular, to azeotrope or azeotrope-like compositions comprising trifluoroiodomethane ($CF_3I$) and trifluoroacetyl chloride ($CF_3COCl$).

BACKGROUND

Fluorocarbon based fluids have found widespread use in industry in a number of applications, including as refrigerants, aerosol propellants, blowing agents, heat transfer media, gaseous dielectrics, and fire suppression.

However, certain compounds such as chlorofluorocarbons (CFCs) and hydrochlorofluorocarbons (HCFCs) are suspected of depleting atmospheric ozone and, thus, are harmful to the environment. Moreover, some of these compounds are believed to contribute to global warming. Accordingly, it is desirable to use fluorocarbon fluids having low or even zero ozone depletion potential, such as hydrofluorocarbons (HFCs), or those with a photolyzable carbon iodine bond, which exhibit short atmospheric lifetime when released at ground level. The use of single component fluids or azeotrope mixtures, which do not fractionate on boiling and evaporation, is also desirable.

Unfortunately, the identification of new, environmentally-safe, non-fractionating mixtures is complicated due to the fact that azeotrope formation is not predictable.

The industry is continually seeking new fluorocarbon-based mixtures that offer alternatives, and are considered environmentally safer substitutes for CFCs, HCFCs and HFCs in use today. Of particular interest are iodide containing compounds and other fluorinated compounds, which have low ozone depletion potentials and low global warming potentials. Such mixtures are the subject of this disclosure.

Although iodide containing compounds are of great potential interest, the purification of iodide containing compounds such as trifluoroiodomethane ($CF_3I$) has presented challenges, and techniques for the removal of impurities from trifluoroiodomethane ($CF_3I$) such as, for example, trifluoromethane (HFC-23), are in constant demand. Therefore, separation techniques such as azeotropic distillation, for example, would be highly desirable.

What is needed are compositions and techniques that may be used to prepare iodide containing compounds, such as trifluoroiodomethane ($CF_3I$), of high purity.

SUMMARY

The present disclosure provides azeotrope or azeotrope-like compositions of trifluoroiodomethane ($CF_3I$) and trifluoroacetyl chloride ($CF_3COCl$).

It is well-recognized in the art that it is not possible to predict the formation of azeotropes, and the present inventors have discovered unexpectedly that trifluoroiodomethane ($CF_3I$) and trifluoroacetyl chloride ($CF_3COCl$) form azeotrope or azeotrope-like compositions.

The present disclosure provides a composition comprising an azeotrope or azeotrope-like composition consisting essentially of, or consisting of, effective amounts of trifluoroacetyl chloride ($CF_3COCl$) and trifluoroiodomethane ($CF_3I$). The azeotrope or azeotrope-like composition has a boiling point between about −46.0° C. and about 90.0° C. at a pressure of between about 4.9 psia and about 348 psia, and consists essentially of, or consists of, from about 0.5 wt. % to about 99.0 wt. % trifluoroacetyl chloride ($CF_3COCl$) and from about 1.0 wt. % to about 99.5 wt. % trifluoroiodomethane ($CF_3I$).

The azeotrope or azeotrope-like composition may consist essentially of, or consist of, from about 0.5 wt. % to about 25 wt. % trifluoroacetyl chloride ($CF_3COCl$), from about 2 wt. % to about 21 wt. % trifluoroacetyl chloride ($CF_3COCl$), from about 14 wt. % to about 18 wt. % trifluoroacetyl chloride ($CF_3COCl$) and, in one azeotrope, about 14.87 wt. % trifluoroacetyl chloride ($CF_3COCl$), as well as from about 75 wt. % to about 99.5 wt. % trifluoroiodomethane ($CF_3I$), from about 79 wt. % to about 98 wt. % trifluoroiodomethane ($CF_3I$), from about 82 wt. % to about 86 wt. % trifluoroiodomethane ($CF_3I$) and, in one azeotrope, about 85.13 wt. % trifluoroiodomethane ($CF_3I$). The azeotrope or azeotrope-like composition has a boiling point of about −22.50° C.±0.30° C. at a pressure of about 14.41 psia±0.30 psia.

In other words, the azeotrope or azeotrope-like composition may consist essentially of, or consist of, from about 0.5 wt. % to about 25 wt. % trifluoroacetyl chloride ($CF_3COCl$) and from about 75 wt. % to about 99.5 wt. % trifluoroiodomethane ($CF_3I$), or from about 2 wt. % to about 21 wt. % trifluoroacetyl chloride ($CF_3COCl$) and from about 79 wt. % to about 98 wt. % trifluoroiodomethane ($CF_3I$), or from about 14 wt. % to about 18 wt. % trifluoroacetyl chloride ($CF_3COCl$) and from about 82 wt. % to about 86 wt. % trifluoroiodomethane ($CF_3I$) and, in one azeotrope, about 14.87 wt. % trifluoroacetyl chloride ($CF_3COCl$) and about 85.13 wt. % trifluoroiodomethane ($CF_3I$). The azeotrope or azeotrope-like composition has a boiling point of about −22.50° C.±0.30° C. at a pressure of about 14.41 psia±0.30 psia.

The present disclosure also provides an azeotrope or azeotrope-like composition consisting essentially of trifluoroacetyl chloride ($CF_3COCl$) and trifluoroiodomethane ($CF_3I$) and having a boiling point of about −22.50° C.±0.30° C. at a pressure of about 14.41 psia±0.30 psia.

The present disclosure also provides a method of forming an azeotrope or azeotrope-like composition comprising the step of combining trifluoroacetyl chloride ($CF_3COCl$) and trifluoroiodomethane ($CF_3I$) to form an azeotrope or azeotrope-like composition consisting essentially of, or consisting of, trifluoroacetyl chloride ($CF_3COCl$) and trifluoroiodomethane ($CF_3I$) having a boiling point between about −46.0° C. and about 90.0° C. at a pressure of between about 4.9 psia and about 348 psia. The combining step may comprise combining from about 0.5 wt. % to about 99.0 wt. % trifluoroacetyl chloride ($CF_3COCl$) and from about 1.0 wt. % to about 99.5 wt. % trifluoroiodomethane ($CF_3I$).

The present disclosure also provides a method of forming an azeotrope or azeotrope-like composition comprising the step of combining trifluoroacetyl chloride ($CF_3COCl$) and trifluoroiodomethane ($CF_3I$) to form an azeotrope or azeotrope-like composition consisting essentially of, or consisting of, trifluoroacetyl chloride ($CF_3COCl$) and trifluoroiodomethane ($CF_3I$). The azeotrope or azeotrope-like composition may have a boiling point of about −22.50° C.±0.30° C. at a pressure of about 14.41 psia±0.30 psia.

The present disclosure also provides a method of separating trifluoroacetyl chloride ($CF_3COCl$) and trifluoroiodomethane ($CF_3I$) from a primary composition comprising trifluoroacetyl chloride ($CF_3COCl$), trifluoroiodomethane ($CF_3I$) and at least one impurity, comprising the steps of forming, within the primary composition, a secondary composition which is an azeotrope or azeotrope-like composition consisting essentially of effective amounts of trifluoroacetyl chloride ($CF_3COCl$) and trifluoroiodomethane ($CF_3I$); and separating the secondary composition from the primary composition and the at least one impurity. The forming step may comprise forming, within the primary composition, a secondary composition which is an azeotrope or azeotrope-like composition consisting essentially of from about 0.5 wt. % to about 99.0 wt. % trifluoroacetyl chloride ($CF_3COCl$) and from about 1.0 wt. % to about 99.0 wt. % trifluoroiodomethane ($CF_3I$) and having a boiling point between about −46.0° C. and about 90.0° C. at a pressure of between about 4.9 psia and about 348 psia.

The present disclosure also provides a method of separating trifluoroacetyl chloride ($CF_3COCl$) or trifluoroiodomethane ($CF_3I$) from at least one impurity, comprising the steps of providing a composition which includes one of trifluoroiodomethane ($CF_3I$) and trifluoroacetyl chloride ($CF_3COCl$), together with at least one impurity; adding a sufficient amount of the other of trifluoroiodomethane ($CF_3I$) and trifluoroacetyl chloride ($CF_3COCl$); and subjecting the composition to conditions effective to form a composition which is an azeotrope or azeotrope-like composition consisting essentially of, or consisting of, effective amounts of trifluoroacetyl chloride ($CF_3COCl$) and trifluoroiodomethane ($CF_3I$); and separating the azeotrope or azeotrope-like composition from the impurity by a separation technique such as phase separation, distillation, or fractionation, for example. The conditions effective to form the azeotrope or azeotrope-like composition may comprise providing about 0.5 wt. % to about 99.0 wt. % trifluoroacetyl chloride ($CF_3COCl$) and from about 1.0 wt. % to about 99.0 wt. % trifluoroiodomethane ($CF_3I$) having a boiling point between about −46.0° C. and about 9-0.0° C. at a pressure of between about 4.9 psia and about 348 psia.

The present disclosure also provides a method of separating trifluoroacetyl chloride ($CF_3COCl$) and trifluoroiodomethane ($CF_3I$) from a primary composition comprising trifluoroacetyl chloride ($CF_3COCl$) and trifluoroiodomethane ($CF_3I$), comprising the steps of conveying a feed stream comprising the primary composition to a low-pressure column; collecting a first bottoms product from the low-pressure column, the first bottoms product consisting essentially of trifluoroacetyl chloride ($CF_3COCl$); conveying a first distillate from the low-pressure column to a high-pressure column, the first distillate comprising an azeotrope or azeotrope-like composition consisting essentially of effective amounts of trifluoroacetyl chloride ($CF_3COCl$) and trifluoroiodomethane ($CF_3I$); and collecting a second bottoms product from the high-pressure column, the second bottoms product consisting essentially of trifluoroiodomethane ($CF_3I$). The method may further comprise, after the second collecting step, the additional step of recycling a second distillate from the high-pressure column back to the feed stream comprising the primary composition.

The present disclosure also provides a method of separating trifluoroacetyl chloride ($CF_3COCl$) and trifluoroiodomethane ($CF_3I$) from a primary composition comprising trifluoroacetyl chloride ($CF_3COCl$) and trifluoroiodomethane ($CF_3I$), comprising the steps of conveying a feed stream comprising the primary composition to a high-pressure column; collecting a first bottoms product from the high-pressure column, the first bottoms product consisting essentially of trifluoroiodomethane ($CF_3I$); conveying a first distillate from the high-pressure column to a low-pressure column, the first distillate comprising an azeotrope or azeotrope-like composition consisting essentially of effective amounts of trifluoroacetyl chloride ($CF_3COCl$) and trifluoroiodomethane ($CF_3I$); collecting a second bottoms product from the low-pressure column, the second bottoms product consisting essentially of trifluoroacetyl chloride ($CF_3COCl$). The method may further comprise, after the second collecting step, the additional step of recycling a second distillate from the low-pressure column back to the feed stream comprising the primary composition.

DETAILED DESCRIPTION

It has been found that trifluoroacetyl chloride ($CF_3COCl$) forms homogeneous, minimum boiling azeotrope and azeotrope-like compositions or mixtures with trifluoroiodomethane ($CF_3I$), and the present disclosure provides homogeneous azeotrope or azeotrope-like compositions comprising trifluoroacetyl chloride ($CF_3COCl$) and trifluoroiodomethane ($CF_3I$). The azeotrope or azeotrope-like compositions may consist essentially of trifluoroacetyl chloride ($CF_3COCl$) and trifluoroiodomethane ($CF_3I$), or the azeotrope or azeotrope-like compositions may consist of trifluoroacetyl chloride ($CF_3COCl$) and trifluoroiodomethane ($CF_3I$).

The present inventors have found experimentally that trifluoroacetyl chloride ($CF_3COCl$) and trifluoroiodomethane ($CF_3I$) form an azeotrope or azeotrope-like composition.

An "azeotrope" composition is a unique combination of two or more components. An azeotrope composition can be characterized in various ways. For example, at a given pressure, an azeotrope composition boils at a constant characteristic temperature which is either greater than the higher boiling point component (maximum boiling azeotrope) or less than the lower boiling point component (minimum boiling azeotrope). At this characteristic temperature the same composition will exist in both the vapor and liquid phases. The azeotrope composition does not fractionate upon boiling or evaporation. Therefore, the components of the azeotrope composition cannot be separated during a phase change.

An azeotrope composition is also characterized in that at the characteristic azeotrope temperature, the bubble point pressure of the liquid phase is identical to the dew point pressure of the vapor phase.

The behavior of an azeotrope composition is in contrast with that of a non-azeotrope composition in which during boiling or evaporation, the liquid composition changes to a substantial degree.

For the purposes of the present disclosure, an azeotrope composition is characterized as that composition which boils at a constant characteristic temperature, the temperature being lower (a minimum boiling azeotrope) than the boiling points of the two or more components, and thereby having the same composition in both the vapor and liquid phases.

One of ordinary skill in the art would understand however that at different pressures, both the composition and the boiling point of the azeotrope composition will vary to some extent. Therefore, depending on the temperature and/or pressure, an azeotrope composition can have a variable composition. The skilled person would therefore understand that composition ranges, rather than fixed compositions, can be used to define azeotrope compositions. In addition, an azeotrope may be defined in terms of exact weight percentages of each component of the compositions characterized by a fixed boiling point at a specified pressure.

An "azeotrope-like" composition is a composition of two or more components which behaves substantially as an azeotrope composition. Thus, for the purposes of this disclosure, an azeotrope-like composition is a combination of two or more different components which, when in liquid form under given pressure, will boil at a substantially constant temperature, and which will provide a vapor composition substantially identical to the liquid composition undergoing boiling.

For the purposes of this disclosure, an azeotrope-like composition is a composition or range of compositions which boils at a temperature range of between about −46.0° C. and about 90.0° C. at a pressure of between about 4.9 psia and about 348 psia, including, for example, a composition or range of compositions which boils at a temperature range of about −22.50° C.±0.30° C. at a pressure of about 14.41 psia±0.30 psia.

Azeotrope or azeotrope-like compositions can be identified using a number of different methods.

For the purposes of this disclosure the azeotrope or azeotrope-like composition is identified experimentally using an ebulliometer (Walas, Phase Equilibria in Chemical Engineering, Butterworth-Heinemann, 1985, 533-544). An ebulliometer is designed to provide extremely accurate measurements of the boiling points of liquids by measuring the temperature of the vapor-liquid equilibrium.

The boiling points of each of the components alone are measured at a constant pressure. As the skilled person will appreciate, for a binary azeotrope or azeotrope-like composition, the boiling point of one of the components of the composition is initially measured. The second component of the composition is then added in varying amounts and the boiling point of each of the obtained compositions is measured using the ebulliometer at said constant pressure.

The measured boiling points are plotted against the composition of the tested composition, for example, for a binary azeotrope, the amount of the second component added to the composition, (expressed as either weight % or mole %). The presence of an azeotrope composition can be identified by the observation of a maximum or minimum boiling temperature which is greater or less than the boiling points of any of the components alone.

As the skilled person will appreciate, the identification of the azeotrope or azeotrope-like composition is made by the comparison of the change in the boiling point of the composition on addition of the second component to the first component, relative to the boiling point of the first component. Thus, it is not necessary that the system be calibrated to the reported boiling point of the particular components in order to measure the change in boiling point.

As previously discussed, at the maximum or minimum boiling point, the composition of the vapor phase will be identical to the composition of the liquid phase. The azeotrope-like composition is therefore that composition of components which provides a substantially constant minimum or maximum boiling point, that is a boiling point between about −46.0° C. and about 90.0° C. at a pressure of between about 4.9 psia and about 348 psia, such as, for example, a boiling point of about −22.50° C.±0.30° C. at a pressure of about 14.41 psia±0.30 psia, at which substantially constant boiling point the composition of the vapor phase will be substantially identical to the composition of the liquid phase.

The present disclosure provides an azeotrope or azeotrope-like composition which comprises effective amounts of trifluoroacetyl chloride ($CF_3COCl$) and trifluoroiodomethane ($CF_3I$) to form an azeotrope or azeotrope-like composition. As used herein, the term "effective amount" is an amount of each component which, when combined with the other component, results in the formation of an azeotrope or azeotrope-like mixture.

The present azeotrope or azeotrope-like compositions may consist essentially of combinations of trifluoroacetyl chloride ($CF_3COCl$) and trifluoroiodomethane ($CF_3I$) or consist of combinations of trifluoroacetyl chloride ($CF_3COCl$) and trifluoroiodomethane ($CF_3I$).

As used herein, the term "consisting essentially of", with respect to the components of an azeotrope or azeotrope-like composition or mixture, means the composition contains the indicated components in an azeotrope or azeotrope-like ratio, and may contain additional components provided that the additional components do not form new azeotrope or azeotrope-like systems. For example, azeotrope mixtures consisting essentially of two compounds are those that form binary azeotropes, which optionally may include one or more additional components, provided that the additional components do not render the mixture non-azeotropic and do not form an azeotrope with either or both of the compounds (e.g., do not form a ternary or higher azeotrope).

The present disclosure also provides a method of forming an azeotrope or azeotrope-like composition by mixing, combining, or blending, effective amounts of, trifluoroacetyl chloride ($CF_3COCl$) and trifluoroiodomethane ($CF_3I$). Any of a wide variety of methods known in the art for combining two or more components to form a composition can be used in the present methods. For example, trifluoroacetyl chloride ($CF_3COCl$) and trifluoroiodomethane ($CF_3I$) can be mixed, blended, or otherwise combined by hand and/or by machine, as part of a batch or continuous reaction and/or process, or via combinations of two or more such steps. Both trifluoroacetyl chloride ($CF_3COCl$) and trifluoroiodomethane ($CF_3I$) are commercially available and can be procured from several different vendors. The components can be provided in the required amounts, for example by weighing and then combining the amounts.

The azeotrope or azeotrope-like composition has a boiling point between about −46.0° C. and about 90.0° C. at a pressure of between about 4.9 psia and about 348 psia, and consists essentially of, or consists of, from about 0.5 wt. % to about 99.0 wt. % trifluoroacetyl chloride ($CF_3COCl$) and from about 1.0 wt. % to about 99.5 wt. % trifluoroiodomethane ($CF_3I$).

The azeotrope or azeotrope-like composition having a boiling point between about −46.0° C. and about 90.0° C. at a pressure of between about 4.9 psia and about 348 psia may also consist essentially of, or consist of, about 4.4 wt. %, 10.7 wt. %, 16.9 wt. %, 23.1 wt. %, 29.3 wt. %, 35.5 wt. %, 41.9 wt. %, 48.4 wt. %, 55.1 wt. %, 62.1 wt. %, 69.7 wt. %, 77.9 wt. %, 87.3 wt. %, or 99.0 wt. % trifluoroacetyl chloride (CF$_3$COCl), or within any range defined between any two of the foregoing values, and about 95.6 wt. %, 89.3 wt. %, 83.1 wt. %, 76.9 wt. %, 70.7 wt. %, 64.5 wt. %, 58.1 wt. %, 51.6 wt. %, 44.9 wt. %, 37.9 wt. %, 30.3 wt. %, 22.1 wt. %, or 12.7 wt. % trifluoroiodomethane (CF$_3$I), or within any range defined between any two of the foregoing values.

Further azeotrope compositions include about 99.5 wt. % trifluoroiodomethane (CF$_3$I) and about 0.5 wt. % trifluoroacetyl chloride (CF$_3$COCl) at a temperature of −46.0° C. and a pressure of about 4.9 psia; about 95.6 wt. % trifluoroiodomethane (CF$_3$I) and about 4.4 wt. % trifluoroacetyl chloride (CF$_3$COCl) at a temperature of −40.0° C. and a pressure of about 6.6 psia; about 89.3 wt. % trifluoroiodomethane (CF$_3$I) and about 10.7 wt. % trifluoroacetyl chloride (CF$_3$COCl) at a temperature of −30.0° C. and a pressure of about 10.5 psia; about 83.1 wt. % trifluoroiodomethane (CF$_3$I) and about 16.9 wt. % trifluoroacetyl chloride (CF$_3$COCl) at a temperature of −20.0° C. and a pressure of about 16.0 psia; about 76.9 wt. % trifluoroiodomethane (CF$_3$I) and about 23.1 wt. % trifluoroacetyl chloride (CF$_3$COCl) at a temperature of −10.0° C. and a pressure of about 23.5 psia; about 70.7 wt. % trifluoroiodomethane (CF$_3$I) and about 29.3 wt. % trifluoroacetyl chloride (CF$_3$COCl) at a temperature of 0.0° C. and a pressure of about 33.7 psia; about 64.5 wt. % trifluoroiodomethane (CF$_3$I) and about 35.5 wt. % trifluoroacetyl chloride (CF$_3$COCl) at a temperature of 10.0° C. and a pressure of about 46.9 psia; about 58.1 wt. % trifluoroiodomethane (CF$_3$I) and about 41.9 wt. % trifluoroacetyl chloride (CF$_3$COCl) at a temperature of 20.0° C. and a pressure of about 63.9 psia; about 51.6 wt. % trifluoroiodomethane (CF$_3$I) and about 48.4 wt. % trifluoroacetyl chloride (CF$_3$COCl) at a temperature of 30.0° C. and a pressure of about 85.1 psia; about 44.9 wt. % trifluoroiodomethane (CF$_3$I) and about 55.1 wt. % trifluoroacetyl chloride (CF$_3$COCl) at a temperature of 40.0° C. and a pressure of about 111.4 psia; about 37.9 wt. % trifluoroiodomethane (CF$_3$I) and about 62.1 wt. % trifluoroacetyl chloride (CF$_3$COCl) at a temperature of 50.0° C. and a pressure of about 143.5 psia; about 30.3 wt. % trifluoroiodomethane (CF$_3$I) and about 69.7 wt. % trifluoroacetyl chloride (CF$_3$COCl) at a temperature of 60.0° C. and a pressure of about 182.1 psia; about 22.1 wt. % trifluoroiodomethane (CF$_3$I) and about 77.9 wt. % trifluoroacetyl chloride (CF$_3$COCl) at a temperature of 70.0° C. and a pressure of about 228.2 psia; about 12.7 wt. % trifluoroiodomethane (CF$_3$I) and about 87.3 wt. % trifluoroacetyl chloride (CF$_3$COCl) at a temperature of 80.0° C. and a pressure of about 283.1 psia; and about 1.0 wt. % trifluoroiodomethane (CF$_3$I) and about 99.0 wt. % trifluoroacetyl chloride (CF$_3$COCl) at a temperature of 90.0° C. and a pressure of about 348.0 psia.

The azeotrope or azeotrope-like composition may consist essentially of, or consist of, from about 0.5 wt. % to about 25 wt. % trifluoroacetyl chloride (CF$_3$COCl), from about 2 wt. % to about 21 wt. % trifluoroacetyl chloride (CF$_3$COCl), from about 14 wt. % to about 18 wt. % trifluoroacetyl chloride (CF$_3$COCl) and, in one azeotrope, about 14.87 wt. % trifluoroacetyl chloride (CF$_3$COCl), as well as from about 75 wt. % to about 99.5 wt. % trifluoroiodomethane (CF$_3$I), from about 79 wt. % to about 98 wt. % trifluoroiodomethane (CF$_3$I), from about 82 wt. % to about 86 wt. % trifluoroiodomethane (CF$_3$I) and, in one azeotrope, about 85.13 wt. % trifluoroiodomethane (CF$_3$I). The azeotrope or azeotrope-like composition has a boiling point of about −22.50° C.±0.30° C. at a pressure of about 14.41 psia±0.30 psia.

In other words, the azeotrope or azeotrope-like composition may consist essentially of, or consist of, from about 0.5 wt. % to about 25 wt. % trifluoroacetyl chloride (CF$_3$COCl) and from about 75 wt. % to about 99.5 wt. % trifluoroiodomethane (CF$_3$I), or from about 2 wt. % to about 21 wt. % trifluoroacetyl chloride (CF$_3$COCl) and from about 79 wt. % to about 98 wt. % trifluoroiodomethane (CF$_3$I), or from about 14 wt. % to about 18 wt. % trifluoroacetyl chloride (CF$_3$COCl) and from about 82 wt. % to about 86 wt. % trifluoroiodomethane (CF$_3$I) and, in one azeotrope, about 14.87 wt. % trifluoroacetyl chloride (CF$_3$COCl) and about 85.13 wt. % trifluoroiodomethane (CF$_3$I). The azeotrope or azeotrope-like composition has a boiling point of about −22.50° C.±0.30° C. at a pressure of about 14.41 psia±0.30 psia.

Stated alternatively, the azeotrope or azeotrope-like composition consists essentially of, or consists of, as little as about 0.5 wt. %, about 2 wt. % or about 14 wt. %, or as great as about 18 wt. %, about 21 wt. % or about 25 wt. % trifluoroacetyl chloride (CF$_3$COCl), or within any range defined between any two of the foregoing values, and the azeotrope or azeotrope-like composition consists essentially of, or consists of, as little as about 75 wt. %, about 79 wt. % or about 82 wt. %, or as great as about 86 wt. %, about 98 wt. % or about 99.5 wt. % trifluoroiodomethane (CF$_3$I), or within any range defined between any two of the foregoing values. The azeotrope composition consists essentially of, or consists of, about 14.87 wt. % and trifluoroacetyl chloride (CF$_3$COCl) and about 85.13 wt. % of trifluoroiodomethane (CF$_3$I). The azeotrope or azeotrope-like composition of the present disclosure has a boiling point of about −22.50° C.±0.30° C. at a pressure of about 14.41 psia±0.30 psia.

The present disclosure also provides a composition comprising the azeotrope or azeotrope-like composition. For example, there is provided a composition comprising at least about 14 wt. % of the azeotrope or azeotrope-like compositions, or at least about 21 wt. % of the azeotrope or azeotrope-like compositions, or at least about 25 wt. % of the azeotrope or azeotrope-like compositions, or at least about 70 wt. % of the azeotrope or azeotrope-like compositions, or at least about 90 wt. % of the azeotrope or azeotrope-like compositions.

The azeotrope or azeotrope-like composition comprising, consisting essentially of, or consisting of effective amounts of trifluoroacetyl chloride (CF$_3$COCl) and trifluoroiodomethane (CF$_3$I) disclosed herein may be used for separating impurities from trifluoroacetyl chloride (CF$_3$COCl) and/or trifluoroiodomethane (CF$_3$I). One impurity that may be present in trifluoroiodomethane (CF$_3$I) is trifluoromethane (HFC-23).

The preparation of azeotropic or azeotrope-like compositions comprising, consisting essentially of, or consisting of effective amounts of trifluoroacetyl chloride (CF$_3$COCl) and trifluoroiodomethane (CF$_3$I) allows separation techniques such as azeotropic distillation, for example, to be used to remove impurities from trifluoroiodomethane (CF$_3$I) to provide trifluoroiodomethane (CF$_3$I) of high purity.

In particular, an azeotrope or azeotrope-like composition comprising, consisting essentially of, or consisting of effective amounts of trifluoroacetyl chloride (CF$_3$COCl) and trifluoroiodomethane (CF$_3$I) may be formed from a composition including one or both of trifluoroacetyl chloride (CF$_3$COCl) and trifluoroiodomethane (CF$_3$I) together with one or more other chemical compounds other than trifluoroacetyl chloride (CF$_3$COCl) and trifluoroiodomethane (CF$_3$I), such as impurities. One such impurity is trifluoromethane (HFC-23), for example. Following the formation of the azeotrope or azeotrope-like composition, the azeotrope or azeotrope-like composition may be separated from the other chemical compounds by a suitable method, such as by distillation, phase separation, or fractionation.

In one example, the present disclosure provides a method of separating trifluoroacetyl chloride ($CF_3COCl$) as an impurity from a primary, crude composition of trifluoroiodomethane ($CF_3I$) which includes trifluoroacetyl chloride ($CF_3COCl$) as an impurity together with at least one additional impurity, comprising the steps of providing a primary composition of crude trifluoroiodomethane ($CF_3I$), trifluoroacetyl chloride ($CF_3COCl$) as an impurity, and at least one additional impurity, and subjecting the primary composition to conditions effective to form a secondary composition which is an azeotrope or azeotrope-like composition consisting essentially of, or consisting of, effective amounts of trifluoroacetyl chloride ($CF_3COCl$) and trifluoroiodomethane ($CF_3I$), and separating the secondary composition from the primary composition by a separation technique such as phase separation, distillation, or fractionation, for example. Thereafter, the secondary composition may be subjected to further separation or purification steps to obtain purified trifluoroiodomethane ($CF_3I$).

In another example, a composition may be provided which includes one of trifluoroiodomethane ($CF_3I$) and trifluoroacetyl chloride ($CF_3COCl$), together with at least one impurity. To this composition, the other of trifluoroiodomethane ($CF_3I$) and trifluoroacetyl chloride ($CF_3COCl$) is added in a sufficient amount and the composition is subjected to conditions effective to form a composition which is an azeotrope or azeotrope-like composition consisting essentially of, or consisting of, effective amounts of trifluoroacetyl chloride ($CF_3COCl$) and trifluoroiodomethane ($CF_3I$), followed by separating the azeotrope or azeotrope-like composition from the impurity by a separation technique such as phase separation, distillation, or fractionation, for example. Thereafter, the azeotrope or azeotrope-like composition of trifluoroiodomethane ($CF_3I$) and trifluoroacetyl chloride ($CF_3COCl$) may be subjected to further separation or purification steps to obtain purified trifluoroiodomethane ($CF_3I$).

In another example discussed in detail below in Example 3, the pressure sensitivity of the present azeotropic compositions allows the separation of compositions including trifluoroacetyl chloride ($CF_3COCl$) and trifluoroiodomethane ($CF_3I$) to form essentially pure compositions of each of trifluoroacetyl chloride ($CF_3COCl$) and trifluoroiodomethane ($CF_3I$) by "pressure swing" distillation.

One method of separating trifluoroacetyl chloride ($CF_3COCl$) and trifluoroiodomethane ($CF_3I$) from a primary composition including trifluoroacetyl chloride ($CF_3COCl$) and trifluoroiodomethane ($CF_3I$) includes the initial step of conveying a feed stream including the primary composition to a low-pressure column. A bottoms product may be collected from the low-pressure column which consists essentially of pure trifluoroacetyl chloride ($CF_3COCl$). A first distillate is then conveyed from the low-pressure column to a high-pressure column, where the first distillate is an azeotrope or azeotrope-like composition consisting essentially of effective amounts of trifluoroacetyl chloride ($CF_3COCl$) and trifluoroiodomethane ($CF_3I$). A second bottoms product may be collected from the high-pressure column which consists essentially of pure trifluoroiodomethane ($CF_3I$). The method may further include, after the second collecting step, the additional step of recycling the second distillate from the high-pressure column back to the feed stream comprising the primary composition.

Similarly, another method of separating trifluoroacetyl chloride ($CF_3COCl$) and trifluoroiodomethane ($CF_3I$) from a primary composition including trifluoroacetyl chloride ($CF_3COCl$) and trifluoroiodomethane ($CF_3I$) includes the initial step of conveying a feed stream including the primary composition to a high-pressure column. A bottoms product may be collected from the high-pressure column which consists essentially of pure trifluoroiodomethane ($CF_3I$). A first distillate is then conveyed from the high-pressure column to a low-pressure column, where the first distillate is an azeotrope or azeotrope-like composition consisting essentially of effective amounts of trifluoroacetyl chloride ($CF_3COCl$) and trifluoroiodomethane ($CF_3I$). A second bottoms product may be collected from the low-pressure column which consists essentially of trifluoroacetyl chloride ($CF_3COCl$). The method may further include, after the second collecting step, the additional step of recycling a second distillate from the low-pressure column back to the feed stream comprising the primary composition.

The following non-limiting Examples serve to illustrate the disclosure.

EXAMPLES

Example 1

Ebulliometer Study

An ebulliometer was used to measure azeotrope and azeotrope-like compositions of trifluoroacetyl chloride ($CF_3COCl$) and trifluoroiodomethane ($CF_3I$). The ebulliometer included a vacuum jacketed glass vessel which was sealed at the bottom and open to the atmosphere at the top. The top, or condenser jacket, of the ebulliometer was filled with a mixture of dry ice and ethanol to attain a temperature of about $-72°$ C., which is significantly lower than the saturation temperature of $-20.2°$ C. for trifluoroacetyl chloride ($CF_3COCl$) and $-22.4°$ C. for trifluoroiodomethane ($CF_3I$) at a pressure of 14.4 psia. In this manner, it was ensured that all vapors in the system were condensed and flowed back into the ebulliometer such that the liquid and vapor phases were in equilibrium. A quartz-platinum thermometer with an accuracy of $±0.002°$ C. was inserted inside the glass vessel and used to determine the temperature of the condensed vapor corresponding to the equilibrium boiling point of the mixture. Boiling chips were used to assist with maintaining a smooth boiling of the mixture in the ebulliometer.

The following procedure was used.

1. The quartz thermometer was immersed into a long dewar which contained an ice/water slurry and it was verified that the thermometer read $0°$ C. The dewar was deep enough so that at least ¾ the length of the thermometer shaft was immersed in the ice/water. The thermometer resistance was recorded in ohms.

2. The condenser jacket was loaded to ¼ full with ethanol. The condenser jacket was cooled by slowly introducing dry ice to avoid boiling over and/or splashing of the ethanol.

3. A known amount of trifluoroiodomethane ($CF_3I$) or trifluoroacetyl chloride ($CF_3COCl$) was added to the ebulliometer and brought to a vigorously refluxing condition. The temperature and atmospheric pressure were recorded using a barometer with a temperature indicator.

The measurement was carried out in two steps. In a first step, about 24.15 g of trifluoroiodomethane ($CF_3I$) having a purity of 99.88 area % as determined by gas chromatography (GC) was first introduced to the ebulliometer by weighing the container before and after the addition using a balance having an accuracy of ±0.01 g. The liquid was brought to a boil and the equilibrium temperature of the trifluoroiodomethane ($CF_3I$) was recorded at the recorded barometric pressure. Then, trifluoroacetyl chloride ($CF_3COCl$) having a purity of 98 area % as determined by gas chromatography (GC) was introduced in small increments into the ebulliometer and the equilibrium temperature of the condensed liquid mixture was recorded.

In a second step, about 15.66 g of trifluoroacetyl chloride ($CF_3COCl$) having a purity of 98 area % as determined by gas chromatography (GC) was introduced to the ebulliometer by weighing the container before and after the addition using a balance having an accuracy of ±0.01 g. The liquid was brought to a boil and the equilibrium temperature of the trifluoroacetyl chloride ($CF_3COCl$) was recorded at the recorded barometric pressure. Then, trifluoroiodomethane ($CF_3I$) having a purity of 99.88 area % as determined by gas chromatography (GC) was introduced in small increments into the ebulliometer and the equilibrium temperature of the condensed liquid mixture was recorded.

Figure 1:
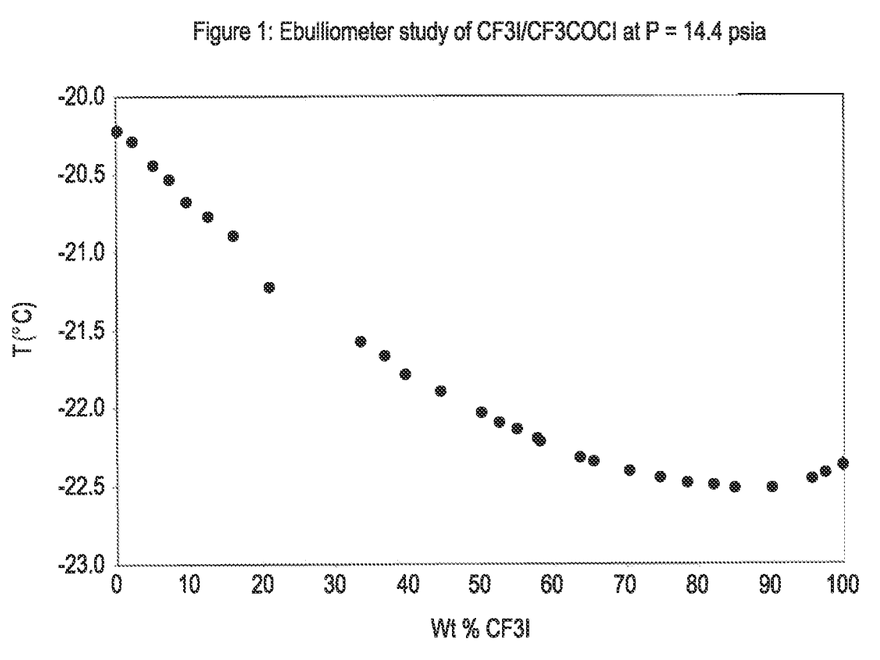
FIG. 1 is a plot of temperature vs. weight percent trifluoroiodomethane ($CF_3I$) measured according to Example 1.

Data from the above first and second steps was combined to complete the composition range data from 0 to 100 weight percent of each of the trifluoroacetyl chloride ($CF_3COCl$) and the trifluoroiodomethane ($CF_3I$) presented below in Table 1, which shows a minimum in temperature which indicates that an azeotrope had been formed, and this data is also presented in graphic form in FIG. 1. The bubble point temperature of the mixture remained constant indicating that the mixture was azeotrope-like over a large composition range.

TABLE 1

Ebulliometer Study of $CF_3I$/Trifluoroacetyl Chloride at P = 14.4 psia

| Temp. (° C.) | Weight % $CF_3I$ | Weight % $CF_3COCl$ |
| --- | --- | --- |
| −22.36 | 100.00 | 0.00 |
| −22.41 | 97.58 | 2.42 |
| −22.45 | 95.80 | 4.20 |
| −22.50 | 90.25 | 9.75 |
| −22.51 | 85.13 | 14.87 |
| −22.49 | 82.28 | 17.72 |
| −22.47 | 78.66 | 21.34 |
| −22.44 | 74.95 | 25.05 |
| −22.40 | 70.68 | 29.32 |
| −22.34 | 65.75 | 34.25 |
| −22.31 | 63.84 | 36.16 |
| −22.21 | 58.36 | 41.64 |
| −22.13 | 55.24 | 44.76 |
| −22.20 | 58.02 | 41.98 |
| −22.09 | 52.73 | 47.27 |
| −22.03 | 50.27 | 49.73 |
| −21.89 | 44.55 | 55.45 |
| −21.78 | 39.65 | 60.35 |
| −21.67 | 36.80 | 63.20 |
| −21.58 | 33.53 | 66.47 |
| −21.23 | 20.95 | 79.05 |
| −20.90 | 15.94 | 84.06 |
| −20.78 | 12.47 | 87.53 |
| −20.68 | 9.53 | 90.47 |
| −20.54 | 7.17 | 92.83 |
| −20.45 | 4.92 | 95.08 |
| −20.30 | 2.06 | 97.94 |
| −20.23 | 0.00 | 100.00 |

Example 2

Azeotrope Locus

In E. W. Lemmon et al., *A Generalized Model for the Thermodynamic Properties of Mixtures*, International Journal of Thermophysics, Vol. 20, pp. 825-835 (1999), the authors describe a method for accurately characterizing the thermodynamic properties of mixtures. The proposed Helmholtz Energy Equation of State (HEOS) considers pure component and interaction parameters of mixture constituents to determine any thermodynamic quantity including mixture vapor and liquid equilibrium compositions which are used for identifying the existence and composition of azeotropes. After reducing the ebulliometer measurements of Example 1 into the HEOS interaction parameters described on page 828 of the foregoing publication, incorporating the pure component thermodynamic properties of both trifluoroiodomethane ($CF_3I$) and trifluoroacetyl chloride ($CF_3COCl$), and evaluating the vapor-liquid equilibrium compositions using the thermodynamic relationships described on page 830-831 of the foregoing publication, it was discovered that the azeotropic composition is unusually sensitive to the system temperature and pressure.

For example, at the system pressure of the ebulliometer in Example 1 (14.4 psia), the azeotropic composition was identified at about 85 wt. % $CF_3I$. However, at an increased system pressure of about 47 psia, the azeotropic composition moves closer to 65 wt. % of trifluoroiodomethane ($CF_3I$). While not wishing to be bound by theory, the sensitivity of the azeotrope to system conditions appears to be a consequence of the relative volatilities between trifluoroiodomethane ($CF_3I$) and trifluoroacetyl chloride ($CF_3COCl$). Examining the VLE of these components as a function of different system conditions yields a locus of azeotropes, shown in Table 2.

TABLE 2

Azeotrope Locus

| Temp. | Pressure | Azeotropic Composition | |
| --- | --- | --- | --- |
| (° C.) | (psia) | Wt. % $CF_3I$ | Wt.% $CF_3COCl$ |
| −46.0 | 4.9 | 99.5 | 0.5 |
| −40.0 | 6.6 | 95.6 | 4.4 |
| −30.0 | 10.5 | 89.3 | 10.7 |
| −20.0 | 16.0 | 83.1 | 16.9 |
| −10.0 | 23.5 | 76.9 | 23.1 |
| 0.0 | 33.7 | 70.7 | 29.3 |
| 10.0 | 46.9 | 64.5 | 35.5 |
| 20.0 | 63.9 | 58.1 | 41.9 |
| 30.0 | 85.1 | 51.6 | 48.4 |
| 40.0 | 111.4 | 44.9 | 55.1 |
| 50.0 | 143.5 | 37.9 | 62.1 |
| 60.0 | 182.1 | 30.3 | 69.7 |
| 70.0 | 228.2 | 22.1 | 77.9 |
| 80.0 | 283.1 | 12.7 | 87.3 |
| 90.0 | 348.0 | 1.0 | 99.0 |

Example 3

Pressure Swing Separation

A well-known consequence of azeotropic mixtures is the inability to fully separate its constituents in a single distillation operation. For example, separation of a 50/50 wt. % mixture of trifluoroiodomethane ($CF_3I$) and trifluoroacetyl chloride ($CF_3COCl$) by a distillation column held at 14.4 psia, exhibiting azeotropic behavior as described by Example 1, would be bounded by compositions between the pure trifluoroacetyl chloride ($CF_3COCl$) (i.e., 0 wt. % trifluoroiodomethane ($CF_3I$)) endpoint and the minimum boiling azeotropic composition (about 85 wt. % trifluoroiodomethane ($CF_3I$)). In other words, distillation of a mixture at these conditions would be unable to produce trifluoroiodomethane ($CF_3I$) in a purity greater than 85 wt. %. To address this fundamental barrier of azeotropes and attain both purer trifluoroiodomethane ($CF_3I$) and trifluoroacetyl chloride ($CF_3COCl$), a different separation strategy must be realized.

As noted by Example 2, the azeotropic composition of binary mixtures of trifluoroiodomethane ($CF_3I$) and trifluoroacetyl chloride ($CF_3COCl$) was discovered to be unusually sensitive to the system conditions. This sensitivity can be exploited to support better separation through pressure swing distillation. In this system, a pressure-sensitive azeotrope is separated using two distillation columns in sequence, one at an arbitrary, relatively lower pressure and one at an arbitrary, relatively higher pressure. The columns may be disposed such that the lower pressure column is first in the sequence. Alternatively, the higher pressure column may be first in the sequence. For the purposes of this example, with reference to FIGS. 2 and 3, the columns are disposed with the lower pressure column first in the sequence.

Figure 2:
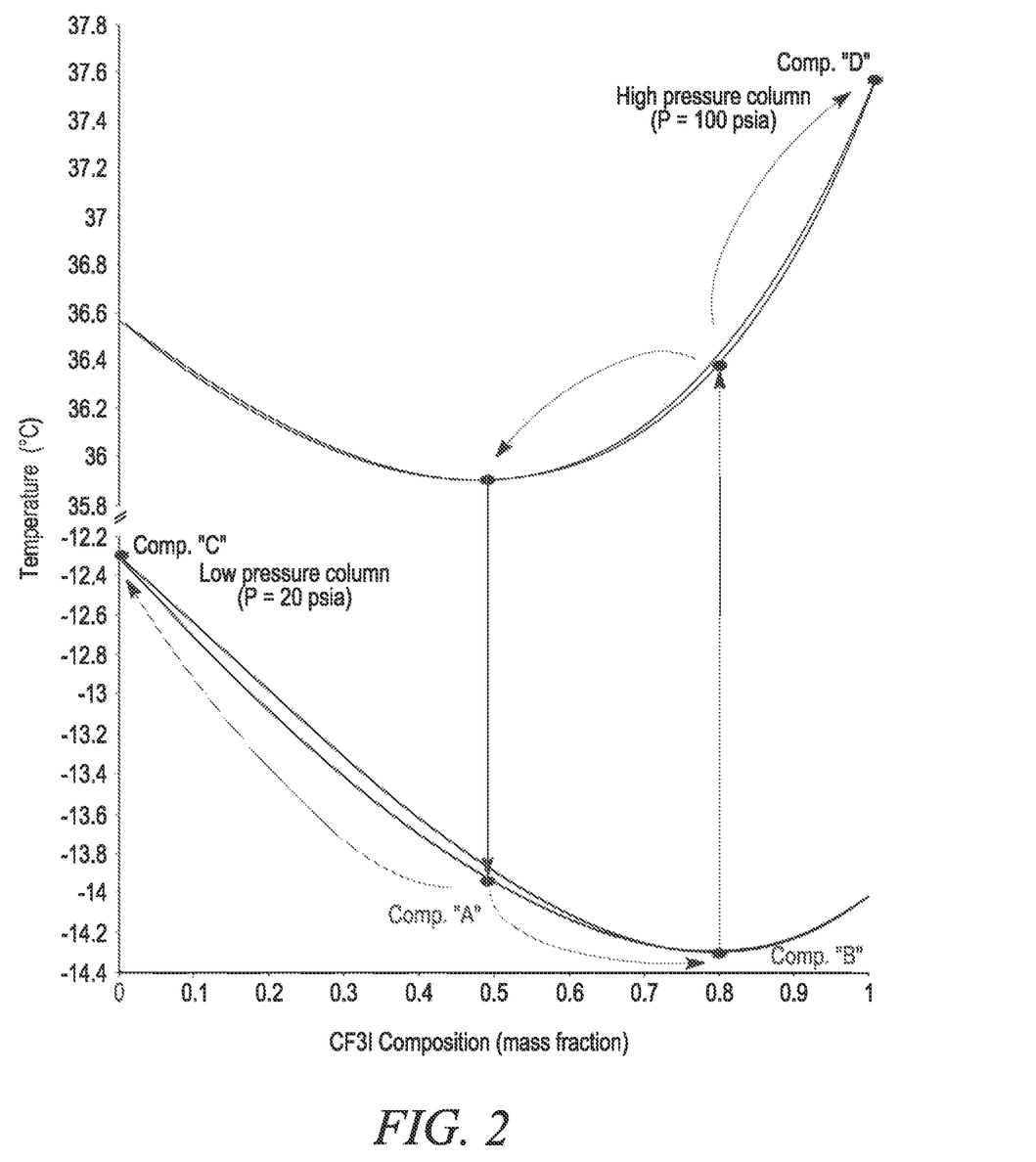
FIG. 2 corresponds to Example 3 and is a plot of temperature versus composition (mass fraction of trifluoroiodomethane ($CF_3I$)) with two curves placed at an arbitrary low-pressure and at an arbitrary high-pressure, respectively.
Figure 3:
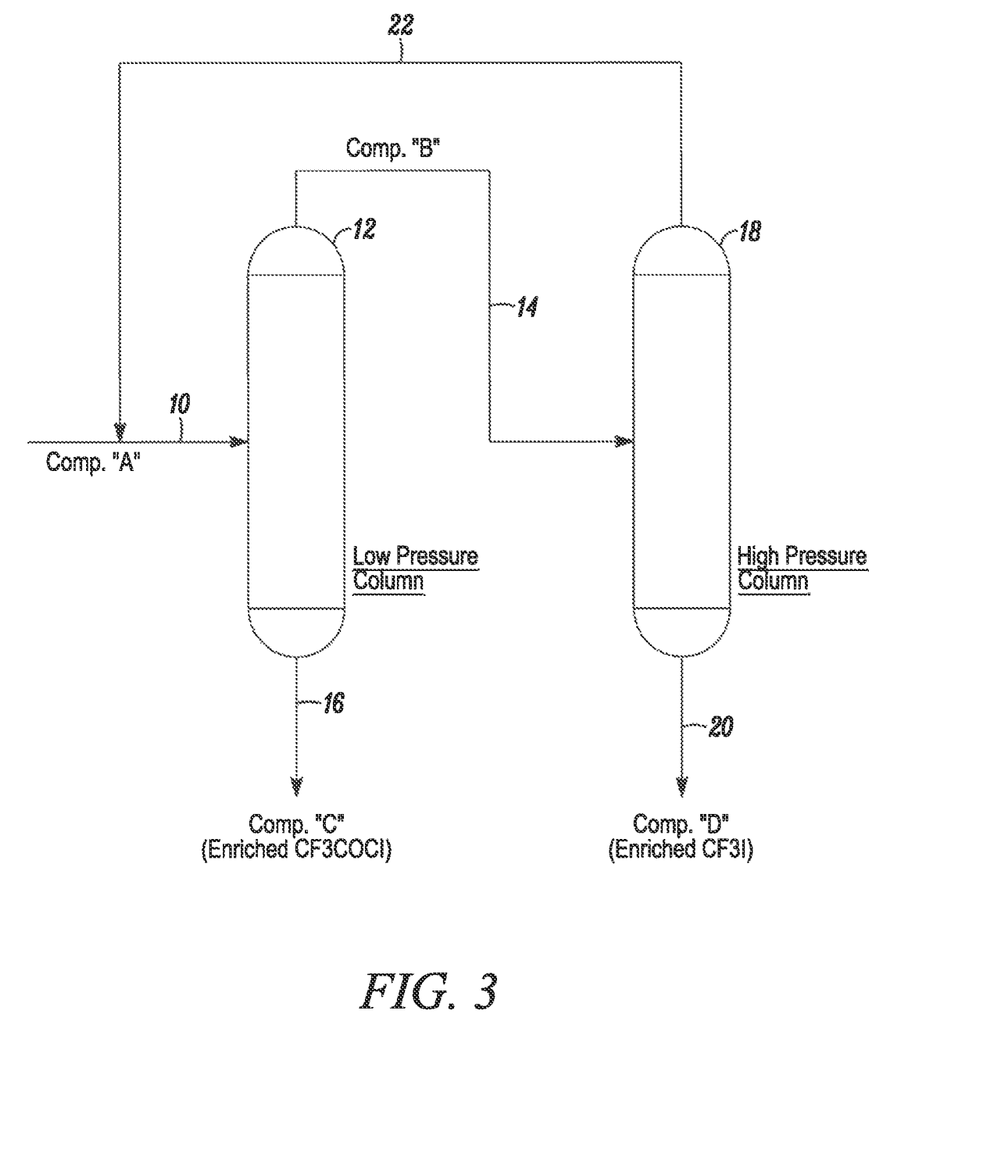
FIG. 3 shows an exemplary pressure swing distillation configuration.

A mixture of trifluoroiodomethane ($CF_3I$) and trifluoroacetyl chloride ($CF_3COCl$) is first subjected to distillation at a lower pressure. The particular composition of the mixture may be tailored as needed. For the purposes of this representative example, a mixture comprising 50 wt. % trifluoroiodomethane ($CF_3I$) and 50 wt. % trifluoroacetyl chloride ($CF_3COCl$) is used. Referring now to FIG. 2, this mixture is designated Composition A ("Comp. 'A'"). Referring now to FIG. 3, the mixture, stream 10, is fed to a distillation column 12 at an arbitrary low-pressure (20 psia for the purposes of this Example).

As shown in FIG. 2, Composition A (stream 10 in FIG. 3) has not yet reached the azeotrope point. As such, the mixture may be separated into fractions enriched in one component of the mixture and the azeotrope or azeotrope-like composition. Here, fractions enriched in the higher boiling point component, trifluoroacetyl chloride ($CF_3COCl$), are collected as the bottoms product and are designated as Composition C ("Comp. 'C'") in FIGS. 2 and 3, and stream 16 in FIG. 3. The azeotrope or azeotrope-like composition is designated as Composition B ("Comp. 'B'") in FIGS. 2 and 3 and is the distillate from the low-pressure column 12 shown in FIG. 3. This mixture is then passed to a column 14 at an arbitrary higher pressure (100 psia for the purposes of this Example), following stream 14 in FIG. 3.

Referring now to FIG. 2, the point representing Composition B in the high-pressure curve is now on the other side of the azeotropic composition in comparison to the low-pressure curve. This permits fractions enriched in the other component of the mixture to be collected. In this Example, fractions enriched in trifluoroiodomethane ($CF_3I$) are collected as the bottoms product and are designated as Composition D ("Comp. 'D'") in FIGS. 2 and 3, and stream 20 in FIG. 3. As with the lower pressure column, the distillate comprises the azeotrope or azeotrope-like mixture. This mixture may be recycled back to co-mingle with Composition A following stream 22 in FIG. 3.

In this way, the barrier of the azeotrope is addressed, using the sensitivity of its composition to the column conditions, to produce two streams enriched in both components. It is important to note that the details in this example are meant to be illustrative. Depending on the context of the mixture, the column conditions and configurations can be designed to support nearly any desired purities of trifluoroiodomethane ($CF_3I$) and/or trifluoroacetyl chloride ($CF_3COCl$).

Example 4

Separation of Impurities

In this Example, a crude composition of trifluoroiodomethane ($CF_3I$) is provided, including trifluoroacetyl chloride ($CF_3COCl$) as an impurity, along with one or more other impurities such as trifluoromethane (HFC-23). The relative amounts of trifluoroiodomethane ($CF_3I$) and trifluoroacetyl chloride ($CF_3COCl$) are altered if necessary to form sufficient relative amounts and the composition is subjected to distillation at conditions effective to form and separate an azeotrope or azeotrope-like composition of trifluoroiodomethane ($CF_3I$) and trifluoroacetyl chloride ($CF_3COCl$) from the remainder of the composition. The separated azeotrope or azeotrope-like composition of trifluoroiodomethane ($CF_3I$) and trifluoroacetyl chloride ($CF_3COCl$) is removed from the remaining crude composition of trifluoroiodomethane ($CF_3I$) as a light component. The remaining crude composition of trifluoroiodomethane ($CF_3I$) is then subjected to different temperature and pressure conditions wherein the other impurities such as trifluoromethane (HFC-23) may be separated by further distillation to obtain purified trifluoroiodomethane ($CF_3I$).

Example 5

Separation of Impurities

In this example, a composition is provided which includes trifluoroiodomethane ($CF_3I$) and at least one impurity such as trifluoromethane (HFC-23), for example. To this composition, trifluoroacetyl chloride ($CF_3COCl$) is added in a sufficient amount and the composition is subjected to conditions effective to form a composition which is an azeotrope or azeotrope-like composition consisting essentially of, or consisting of, effective amounts of trifluoroacetyl chloride ($CF_3COCl$) and trifluoroiodomethane ($CF_3I$), followed by separating the azeotrope or azeotrope-like composition from the impurity by a separation technique such as phase separation, distillation, or fractionation, for example. Thereafter, the azeotrope or azeotrope-like composition of trifluoroiodomethane ($CF_3I$) and trifluoroacetyl chloride ($CF_3COCl$) may be subjected to further separation or purification steps to obtain purified trifluoroiodomethane ($CF_3I$).

Example 6

Separation of Impurities

In this example, a composition is provided which includes trifluoroacetyl chloride ($CF_3COCl$) and at least one impurity such as trifluoromethane (HFC-23), for example. To this composition, trifluoroiodomethane ($CF_3I$) is added in a sufficient amount and the composition is subjected to conditions effective to form a composition which is an azeotrope or azeotrope-like composition consisting essentially of, or consisting of, effective amounts of trifluoroacetyl chloride ($CF_3COCl$) and trifluoroiodomethane ($CF_3I$), followed by separating the azeotrope or azeotrope-like composition from the impurity by a separation technique such as phase separation, distillation, or fractionation, for example. Thereafter, the azeotrope or azeotrope-like composition of trifluoroiodomethane ($CF_3I$) and trifluoroacetyl chloride ($CF_3COCl$) may be subjected to further separation or purification steps to obtain purified trifluoroiodomethane ($CF_3I$).

ASPECTS

Aspect 1 is an azeotrope or azeotrope-like composition comprising, consisting essentially of, or consisting of effective amounts of trifluoroacetyl chloride ($CF_3COCl$) and trifluoroiodomethane ($CF_3I$).

Aspect 2 is the azeotrope or azeotrope-like composition of Aspect 1, wherein the azeotrope or azeotrope-like composition has a boiling point between about −46.0° C. and about 90.0° C. at a pressure of between about 4.9 psia and about 348 psia.

Aspect 3 is the azeotrope or azeotrope-like composition of Aspects 1 or 2, wherein the azeotrope or azeotrope-like composition consists essentially of from about 0.5 wt. % to about 99.0 wt. % trifluoroacetyl chloride ($CF_3COCl$) and from about 1.0 wt. % to about 99.5 wt. % trifluoroiodomethane ($CF_3I$).

Aspect 4 is an azeotrope composition including about 99.5 wt. % trifluoroiodomethane ($CF_3I$) and about 0.5 wt. % trifluoroacetyl chloride ($CF_3COCl$) at a temperature of −46.0° C. and a pressure of about 4.9 psia.

Aspect 5 is an azeotrope composition including about 95.6 wt. % trifluoroiodomethane ($CF_3I$) and about 4.4 wt. % trifluoroacetyl chloride ($CF_3COCl$) at a temperature of −40.0° C. and a pressure of about 6.6 psia.

Aspect 6 is an azeotrope composition including about 89.3 wt. % trifluoroiodomethane ($CF_3I$) and about 10.7 wt. % trifluoroacetyl chloride ($CF_3COCl$) at a temperature of −30.0° C. and a pressure of about 10.5 psia.

Aspect 7 is an azeotrope composition including about 83.1 wt. % trifluoroiodomethane ($CF_3I$) and about 16.9 wt. % trifluoroacetyl chloride ($CF_3COCl$) at a temperature of −20.0° C. and a pressure of about 16.0 psia.

Aspect 8 is an azeotrope composition including about 76.9 wt. % trifluoroiodomethane ($CF_3I$) and about 23.1 wt. % trifluoroacetyl chloride ($CF_3COCl$) at a temperature of −10.0° C. and a pressure of about 23.5 psia.

Aspect 9 is an azeotrope composition including about 70.7 wt. % trifluoroiodomethane ($CF_3I$) and about 29.3 wt. % trifluoroacetyl chloride ($CF_3COCl$) at a temperature of 0.0° C. and a pressure of about 33.7 psia.

Aspect 10 is an azeotrope composition including about 64.5 wt. % trifluoroiodomethane ($CF_3I$) and about 35.5 wt. % trifluoroacetyl chloride ($CF_3COCl$) at a temperature of 10.0° C. and a pressure of about 46.9 psia.

Aspect 11 is an azeotrope composition including about 58.1 wt. % trifluoroiodomethane ($CF_3I$) and about 41.9 wt. % trifluoroacetyl chloride ($CF_3COCl$) at a temperature of 20.0° C. and a pressure of about 63.9 psia.

Aspect 12 is an azeotrope composition including about 51.6 wt. % trifluoroiodomethane ($CF_3I$) and about 48.4 wt. % trifluoroacetyl chloride ($CF_3COCl$) at a temperature of 30.0° C. and a pressure of about 85.1 psia.

Aspect 13 is an azeotrope composition including about 44.9 wt. % trifluoroiodomethane ($CF_3I$) and about 55.1 wt. % trifluoroacetyl chloride ($CF_3COCl$) at a temperature of 40.0° C. and a pressure of about 111.4 psia.

Aspect 14 is an azeotrope composition including about 37.9 wt. % trifluoroiodomethane ($CF_3I$) and about 62.1 wt. % trifluoroacetyl chloride ($CF_3COCl$) at a temperature of 50.0° C. and a pressure of about 143.5 psia.

Aspect 15 is an azeotrope composition including about 30.3 wt. % trifluoroiodomethane ($CF_3I$) and about 69.7 wt. % trifluoroacetyl chloride ($CF_3COCl$) at a temperature of 60.0° C. and a pressure of about 182.1 psia.

Aspect 16 is an azeotrope composition including about 22.1 wt. % trifluoroiodomethane ($CF_3I$) and about 77.9 wt. % trifluoroacetyl chloride ($CF_3COCl$) at a temperature of 70.0° C. and a pressure of about 228.2 psia.

Aspect 17 is an azeotrope composition including about 12.7 wt. % trifluoroiodomethane ($CF_3I$) and about 87.3 wt. % trifluoroacetyl chloride ($CF_3COCl$) at a temperature of 80.0° C. and a pressure of about 283.1 psia.

Aspect 18 is an azeotrope composition including about 1.0 wt. % trifluoroiodomethane ($CF_3I$) and about 99.0 wt. % trifluoroacetyl chloride ($CF_3COCl$) at a temperature of 90.0° C. and a pressure of about 348.0 psia.

Aspect 19 is the azeotrope or azeotrope-like composition of Aspect 1, comprising, consisting essentially of, or consisting of from about 0.5 wt. % to about 25 wt. % trifluoroacetyl chloride ($CF_3COCl$) and from about 75 wt. % to about 99.5 wt. % trifluoroiodomethane ($CF_3I$).

Aspect 20 is the azeotrope or azeotrope-like composition of Aspect 19, comprising, consisting essentially of, or consisting of from about 2 wt. % to about 21 wt. % trifluoroacetyl chloride ($CF_3COCl$) and from about 79 wt. % to about 98 wt. % trifluoroiodomethane ($CF_3I$).

Aspect 21 is the azeotrope or azeotrope-like composition of Aspect 20, comprising, consisting essentially of, or consisting of from about 14 wt. % to about 18 wt. % trifluoroacetyl chloride ($CF_3COCl$) and from about 82 wt. % to about 86 wt. % trifluoroiodomethane ($CF_3I$).

Aspect 22 is the azeotrope or azeotrope-like composition of Aspect 21, comprising, consisting essentially of, or consisting of about 14.87 wt. % trifluoroacetyl chloride ($CF_3COCl$) and about 85.13 wt. % trifluoroiodomethane ($CF_3I$).

Aspect 23 is the azeotrope or azeotrope-like composition of any of Aspects 19 to 22, wherein the composition has a boiling point of about −22.50° C.±0.30° C. at a pressure of about 14.41 psia±0.30 psia.

Aspect 24 is the azeotrope or azeotrope-like composition of any of Aspects 1 to 18, consisting essentially of trifluoroacetyl chloride ($CF_3COCl$) and trifluoroiodomethane ($CF_3I$).

Aspect 25 is the azeotrope or azeotrope-like composition of any of Aspects 1 to 18, consisting of trifluoroacetyl chloride ($CF_3COCl$) and trifluoroiodomethane ($CF_3I$).

Aspect 26 is a composition comprising, consisting essentially of, or consisting of the azeotrope or azeotrope-like composition of any of Aspects 1 to 18.

Aspect 27 is the composition of Aspect 26, comprising, consisting essentially of, or consisting of at least about 5 wt. % of the azeotrope or azeotrope-like composition.

Aspect 28 is the composition of Aspect 27, comprising, consisting essentially of, or consisting of at least about 15 wt. % of the azeotrope or azeotrope-like composition.

Aspect 29 is the composition of Aspect 28, comprising, consisting essentially of, or consisting of at least about 50 wt. % of the azeotrope or azeotrope-like composition.

Aspect 30 is the composition of Aspect 29, comprising, consisting essentially of, or consisting of at least about 70 wt. % of the azeotrope or azeotrope-like composition.

Aspect 31 is the composition of Aspect 30, comprising, consisting essentially of, or consisting of at least about 90 wt. % of the azeotrope or azeotrope-like composition.

Aspect 32 is a method of forming an azeotrope or azeotrope-like composition comprising the step of combining trifluoroacetyl chloride (CF$_3$COCl) and trifluoroiodomethane (CF$_3$I) to form an azeotrope or azeotrope-like composition comprising, consisting essentially of, or consisting of trifluoroacetyl chloride (CF$_3$COCl) and trifluoroiodomethane (CF$_3$I) having a boiling point between about −46.0° C. and about 90.0° C. at a pressure of between about 4.9 psia and about 348 psia.

Aspect 33 is the method of Aspect 32, wherein the combining step comprises combining from about 0.5 wt. % to about 99.0 wt. % trifluoroacetyl chloride (CF$_3$COCl) and from about 1.0 wt. % to about 99.5 wt. % trifluoroiodomethane (CF$_3$I).

Aspect 34 is a method of forming an azeotrope or azeotrope-like composition comprising the step of combining trifluoroacetyl chloride (CF$_3$COCl) and trifluoroiodomethane (CF$_3$I) to form the azeotrope or azeotrope-like composition comprising effective amounts of trifluoroacetyl chloride (CF$_3$COCl) and trifluoroiodomethane (CF$_3$I).

Aspect 35 is the method of Aspect 34, the method comprising the step of combining trifluoroacetyl chloride (CF$_3$COCl) and trifluoroiodomethane (CF$_3$I) to form the azeotrope or azeotrope-like composition of any of Aspects 1 to 18.

Aspect 35 is a method of separating trifluoroacetyl chloride (CF$_3$COCl) and trifluoroiodomethane (CF$_3$I) from a primary composition comprising trifluoroacetyl chloride (CF$_3$COCl), trifluoroiodomethane (CF$_3$I) and at least one impurity, comprising the steps of forming, within the primary composition, a secondary composition which is an azeotrope or azeotrope-like composition comprising, consisting essentially of, or consisting of effective amounts of trifluoroacetyl chloride (CF$_3$COCl) and trifluoroiodomethane (CF$_3$I) having a boiling point between about −46.0° C. and about 9-0.0° C. at a pressure of between about 4.9 psia and about 348 psia; and separating the secondary composition from the primary composition and the at least one impurity.

Aspect 36 is the method of Aspect 35, wherein the forming step comprises forming, within the primary composition, a secondary composition which is an azeotrope or azeotrope-like composition comprising, consisting essentially of, or consisting of from about 0.5 wt. % to about 99.0 wt. % trifluoroacetyl chloride (CF$_3$COCl) and from about 1.0 wt. % to about 99.5 wt. % trifluoroiodomethane (CF$_3$I).

Aspect 37 is the method of Aspect 35 or Aspect 36, wherein the azeotrope or azeotrope-like composition is as defined in any of Aspects 1 to 18.

Aspect 38 is the method of Aspect 35 or Aspect 36, in which the separation is carried out by at least one of phase separation, distillation, and fractionation.

Aspect 39 is a method of separating trifluoroacetyl chloride (CF$_3$COCl) and trifluoroiodomethane (CF$_3$I) from a primary composition comprising trifluoroacetyl chloride (CF$_3$COCl), trifluoroiodomethane (CF$_3$I) and at least one impurity, comprising the steps of forming, within the primary composition, a secondary composition which is an azeotrope or azeotrope-like composition comprising, consisting essentially of, or consisting of effective amounts of trifluoroacetyl chloride (CF$_3$COCl) and trifluoroiodomethane (CF$_3$I); and separating the secondary azeotrope or azeotrope-like composition from the primary composition and the at least one impurity.

Aspect 40 is the method of Aspect 39, wherein the azeotrope or azeotrope-like composition is as defined in any of Aspects 1 to 18.

Aspect 41 is the method of Aspect 39 or Aspect 40, in which the separation is carried out by at least one of phase separation, distillation, and fractionation.

Aspect 42 is a method of separating trifluoroacetyl chloride (CF$_3$COCl) or trifluoroiodomethane (CF$_3$I) from at least one impurity, comprising the steps of providing a composition which includes one of trifluoroiodomethane (CF$_3$I) and trifluoroacetyl chloride (CF$_3$COCl), together with at least one impurity; adding a sufficient amount of the other of trifluoroiodomethane (CF$_3$I) and trifluoroacetyl chloride (CF$_3$COCl) and subjecting the composition to conditions effective to form a composition which is an azeotrope or azeotrope-like composition consisting essentially of, or consisting of, effective amounts of trifluoroacetyl chloride (CF$_3$COCl) and trifluoroiodomethane (CF$_3$I), and separating the azeotrope or azeotrope-like composition from the impurity.

Aspect 43 is the method of Aspect 42, wherein the azeotrope or azeotrope-like composition is as defined in any of Aspects 1 to 18.

Aspect 44 is the method of Aspect 42 or Aspect 43, in which the separation is carried out by at least one of phase separation, distillation, and fractionation.

Aspect 45 is a method of separating trifluoroacetyl chloride (CF$_3$COCl) and trifluoroiodomethane (CF$_3$I) from a primary composition comprising trifluoroacetyl chloride (CF$_3$COCl) and trifluoroiodomethane (CF$_3$I), comprising the steps of conveying a feed stream comprising the primary composition to a low-pressure column; collecting a first bottoms product from the low-pressure column, the first bottoms product consisting essentially of trifluoroacetyl chloride (CF$_3$COCl); conveying a first distillate from the low-pressure column to a high-pressure column, the first distillate comprising, consisting essentially of, or consisting of an azeotrope or azeotrope-like composition consisting essentially of effective amounts of trifluoroacetyl chloride (CF$_3$COCl) and trifluoroiodomethane (CF$_3$I); and collecting a second bottoms product from the high-pressure column, the second bottoms product consisting essentially of trifluoroiodomethane (CF$_3$I).

Aspect 46 is the method of Aspect 45, further comprising, after the second collecting step, the additional step of recycling a second distillate from the high-pressure column back to the feed stream comprising the primary composition.

Aspect 47 is a method of separating trifluoroacetyl chloride (CF$_3$COCl) and trifluoroiodomethane (CF$_3$I) from a primary composition comprising trifluoroacetyl chloride (CF$_3$COCl) and trifluoroiodomethane (CF$_3$I), comprising the steps of conveying a feed stream comprising the primary composition to a high-pressure column; collecting a first bottoms product from the high-pressure column, the first bottoms product consisting essentially of trifluoroiodomethane (CF$_3$I); conveying a first distillate from the high-pressure column to a low-pressure column, the first distillate comprising, consisting essentially of, or consisting of an azeotrope or azeotrope-like composition consisting essentially of effective amounts of trifluoroacetyl chloride (CF$_3$COCl) and trifluoroiodomethane (CF$_3$I); and collecting a second bottoms product from the low-pressure column, the second bottoms product consisting essentially of trifluoroacetyl chloride (CF$_3$COCl)

Aspect 48 is the method of Aspect 47, further comprising, after the second collecting step, the additional step of recycling a second distillate from the low-pressure column back to the feed stream comprising the primary composition.

As used herein, the phrase "within any range defined between any two of the foregoing values" literally means that any range may be selected from any two of the values listed prior to such phrase regardless of whether the values are in the lower part of the listing or in the higher part of the listing. For example, a pair of values may be selected from two lower values, two higher values, or a lower value and a higher value.

As used herein, the singular forms "a", "an" and "the" include plural unless the context clearly dictates otherwise. Moreover, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances that fall within the scope of the appended claims.

What is claimed is:

1. A composition comprising an azeotrope or azeotrope-like composition consisting essentially of effective amounts of trifluoroacetyl chloride ($CF_3COCl$) and trifluoroiodomethane ($CF_3I$).

2. The composition of claim 1, wherein the azeotrope or azeotrope-like composition has a boiling point between about −46.0° C. and about 90.0° C. at a pressure of between about 4.9 psia and about 348 psia.

3. The composition of claim 2, wherein the azeotrope or azeotrope-like composition consists essentially of from about 0.5 wt. % to about 99.0 wt. % trifluoroacetyl chloride ($CF_3COCl$) and from about 1.0 wt. % to about 99.5 wt. % trifluoroiodomethane ($CF_3I$).

4. The composition of claim 1, wherein the azeotrope or azeotrope-like composition has a boiling point of about −22.50° C.±0.30° C. at a pressure of about 14.41 psia±0.30 psia.

5. The composition of claim 2, wherein the azeotrope or azeotrope-like composition consists essentially of from about 0.5 wt. % to about 25 wt. % trifluoroacetyl chloride ($CF_3COCl$) and from about 75 wt. % to about 99.5 wt. % trifluoroiodomethane ($CF_3I$).

6. The composition of claim 2, wherein the azeotrope or azeotrope-like composition consists essentially of from about 2 wt. % to about 21 wt. % trifluoroacetyl chloride ($CF_3COCl$) and from about 79 wt. % to about 98 wt. % trifluoroiodomethane ($CF_3I$).

7. The composition of claim 2, wherein the azeotrope or azeotrope-like composition consists essentially of from about 14 wt. % to about 18 wt. % trifluoroacetyl chloride ($CF_3COCl$) and from about 82 wt. % to about 86 wt. % trifluoroiodomethane ($CF_3I$).

8. The composition of claim 1, comprising an azeotrope or azeotrope-like composition consisting essentially of trifluoroacetyl chloride ($CF_3COCl$) and trifluoroiodomethane ($CF_3I$) and having a boiling point of about −22.50° C.±0.30° C. at a pressure of about 14.41 psia±0.30 psia.

9. The composition of claim 8, wherein the azeotrope or azeotrope-like composition consists essentially of from about 0.5 wt. % to about 25 wt. % trifluoroacetyl chloride ($CF_3COCl$)) and from about 75 wt. % to about 99.5 wt. % trifluoroiodomethane ($CF_3I$).

10. The composition of claim 8, wherein the azeotrope or azeotrope-like composition consists essentially of from about 2 wt. % to about 21 wt. % trifluoroacetyl chloride ($CF_3COCl$) and from about 79 wt. % to about 98 wt. % trifluoroiodomethane ($CF_3I$).

11. The composition of claim 8, wherein the azeotrope or azeotrope-like composition consists essentially of from about 14 wt. % to about 18 wt. % trifluoroacetyl chloride ($CF_3COCl$) and from about 82 wt. % to about 86 wt. % trifluoroiodomethane ($CF_3I$).

12. A method of separating an azeotrope or azeotrope-like mixture of trifluoroacetyl chloride ($CF_3COCl$) and trifluoroiodomethane ($CF_3I$), comprising:
    conveying a feed stream comprising an azeotrope or azeotrope-like composition consisting essentially of effective amounts of trifluoroacetyl chloride ($CF_3COCl$) and trifluoroiodomethane ($CF_3I$) to a low-pressure column to provide a first bottoms product and a first distillate;
    collecting the first bottoms product from the low-pressure column;
    conveying the first distillate from the low-pressure column to a high-pressure column, the first distillate comprising an azeotrope or azeotrope-like composition consisting essentially of effective amounts of trifluoroacetyl chloride ($CF_3COCl$) and trifluoroiodomethane ($CF_3I$); and
    collecting a second bottoms product from the high-pressure column.

13. The method of claim 12, wherein the azeotrope or azeotrope-like composition consists essentially of from about 0.5 wt. % to about 99.0 wt. % trifluoroacetyl chloride ($CF_3COCl$) and from about 1.0 wt. % to about 99.5 wt. % trifluoroiodomethane ($CF_3I$).

14. The method of claim 13, wherein the azeotrope or azeotrope-like composition has a boiling point between about −46.0° C. and about 90.0° C. at a pressure of between about 4.9 psia and about 348 psia.

15. The method of claim 12, wherein the first bottoms product consists essentially of trifluoroacetyl chloride ($CF_3COCl$).

16. The method of claim 12, wherein the second bottoms product consists essentially of trifluoroiodomethane ($CF_3I$).

17. The method of claim 12, wherein the first bottoms product consists essentially of trifluoroiodomethane ($CF_3I$).

18. A method of separating trifluoroacetyl chloride ($CF_3COCl$) and trifluoroiodomethane ($CF_3I$) from a primary composition comprising trifluoroacetyl chloride ($CF_3COCl$), trifluoroiodomethane ($CF_3I$) and at least one impurity, comprising the steps of:
    forming, within the primary composition, a secondary composition which is an azeotrope or azeotrope-like composition consisting essentially of effective amounts of trifluoroacetyl chloride ($CF_3COCl$) and trifluoroiodomethane ($CF_3I$) having a boiling point between about −46.0° C. and about 90.0° C. at a pressure of between about 4.9 psia and about 348 psia; and
    separating the secondary composition from the primary composition and the at least one impurity.

19. The method of claim 18, comprising the additional steps, prior to the forming step, of:
    providing a composition which includes one of trifluoroiodomethane ($CF_3I$) and trifluoroacetyl chloride ($CF_3COCl$), together with at least one impurity; and adding a sufficient amount of the other of trifluoroiodomethane ($CF_3I$) and trifluoroacetyl chloride ($CF_3COCl$).

\* \* \* \* \*